United States Patent [19]
Lafontaine et al.

[11] Patent Number: 5,860,938
[45] Date of Patent: Jan. 19, 1999

[54] MEDICAL PRESSURE SENSING GUIDE WIRE

[75] Inventors: Daniel M. Lafontaine; Dnyanesh Talpade, both of Plymouth; Roger N. Hastings, Maple Grove, all of Minn.

[73] Assignee: Scimed Life Systems, Inc., Maple Grove, Minn.

[21] Appl. No.: 707,829

[22] Filed: Sep. 6, 1996

Related U.S. Application Data

[63] Continuation-in-part of Ser. No. 614,774, Mar. 7, 1996.

[51] Int. Cl.⁶ .......................... A61B 5/0215; A61B 05/021
[52] U.S. Cl. .......................... 600/585; 600/488; 600/486
[58] Field of Search ..................................... 128/637, 657, 128/673, 674, 675, 772; 600/369, 434, 486, 487, 488, 585

[56] References Cited

U.S. PATENT DOCUMENTS

| | | |
|---|---|---|
| 3,724,274 | 4/1973 | Millar . |
| 3,811,427 | 5/1974 | Kresse . |
| 4,545,389 | 10/1985 | Schaberg et al. . |
| 4,554,927 | 11/1985 | Fussell . |
| 4,846,191 | 7/1989 | Brockway et al. . |
| 4,909,796 | 3/1990 | Hagio et al. . |
| 4,928,693 | 5/1990 | Goodin et al. . |
| 4,953,553 | 9/1990 | Tremulis . |
| 4,964,409 | 10/1990 | Tremulis . |
| 5,050,606 | 9/1991 | Tremulis . |
| 5,063,936 | 11/1991 | Sato et al. . |
| 5,065,769 | 11/1991 | de Toledo . |
| 5,184,627 | 2/1993 | de Toledo . |
| 5,197,486 | 3/1993 | Frassica ................................. 128/657 |
| 5,211,636 | 5/1993 | Mische . |
| 5,280,789 | 1/1994 | Potts ........................................ 128/673 |
| 5,282,478 | 2/1994 | Fleischhaker, Jr. et al. ........... 128/772 |
| 5,322,508 | 6/1994 | Viera . |
| 5,450,853 | 9/1995 | Hastings et al. . |
| 5,476,450 | 12/1995 | Ruggio . |
| 5,569,197 | 10/1996 | Helmus et al. . |
| 5,573,007 | 11/1996 | Bobo, Sr. . |

FOREIGN PATENT DOCUMENTS

0419277B1  5/1996  European Pat. Off. .

OTHER PUBLICATIONS

New Product Bulletin, Medi–tech, Cragg Convertible Wire, Mar. 1989.
Products for Regional Thrombolysis, Medi–tech, Katzeen Infusion Wire, Mewissen Infusion Catheter, Cragg Convertible Wire, Jul. 1992.
The Sos Open Ended Guidewire from USCI, Applications & Case Studies, C.R. Bard, Inc., Nov. 1985.
Measuring Principles of Arterial Waves, Wilmer W. Nichols and Michael F. O'Rourke, McDonald's Blood Flow in Arteries, Theorectical, Experimental and Clinical Principles, $3^{4rd}$ Edition, pp. 143–162.
Pressure Measurement, Charles R. Lamber, M.D., Ph.D., Carl J. Pepine, M.D. and Wilmer W. Nichols, Ph.D, Diagnostic and Therapeutic Cardiac Catheterization, pp. 283–297.

Primary Examiner—William E. Kamm
Assistant Examiner—Carl H. Layno
Attorney, Agent, or Firm—Robert A. Atkinson

[57] ABSTRACT

A guide wire that is capable of sensing the phasic pressure at the distal end of the guide wire. The guide wire has a central lumen which provides a non-compliant fluid path from the distal end of the guide wire to a pressure transducer at the proximal end of the guide wire.

13 Claims, 2 Drawing Sheets

MEDICAL PRESSURE SENSING GUIDE WIRE

CROSS REFERENCE TO RELATED APPLICATIONS

This application is a continuation in part of U.S. patent application, Ser. No. 08/614,774 filed on Mar. 7, 1996 and entitled PRESSURE SENSING GUIDE WIRE.

FIELD OF THE INVENTION

The present invention generally relates to a pressure sensor, and more particularly, a guide wire capable of measuring fluid pressure at various places within the human vasculature. Those skilled in the art will recognize the benefits of applying the present invention to similar fields not discussed herein.

BACKGROUND OF THE INVENTION

Pressure measurements made before, after, or during a therapeutic or diagnostic procedure can be important methods of analyzing any body conduit. In blood vessels, pressure measurement may be used to continuously monitor a patient's condition, to determine the patency of a specific artery or vessel, to assess the severity of a lesion or stenosis, or to asses the results of a therapeutic procedure such as angioplasty, atherectomy, or stenting. Pressure measurements may be of two types, phasic or flat line. The flat line pressure is the average of pressure changes over time. The phasic pressure is a wave form. While the average pressure is of interest, physicians can readily identify a true physiologic wave form, with frequency content from DC up to about 30 Hz, and compare it to expected norms, thereby making phasic pressure measurement a highly valuable diagnostic tool.

Percutaneous coronary angioplasty is a specific procedure in which pressure measurement may be a valuable tool for lesion assessment and therapy assessment. The catheter which is used to measure pressure must be small enough so that the catheter itself does not interfere with measurement. In the epicardial coronary arteries, this requires catheters which are a fraction of a millimeter in diameter. It is also preferred to make the pressure measurement from a catheter which is already being used in a procedure, rather than exchanging for a pressure measuring catheter.

Prior art devices disclosed by Hastings, et al. in U.S. Pat. No. 5,450,853, Wise, et al. in U.S. Pat. No. 5,113,868, and Little in U.S. Pat. No. 5,313,957 have integrated microsensors into the distal end of a guide wire with an electrical or optical interconnect extending to the proximal end of the wire (approximately 1.8 meters). Since the wire is only 0.014 inches in outer diameter, it is very difficult to integrate the sensor and interconnect into the guide wire without altering the mechanical performance of the wire. The wire must torque, push, and steer sufficiently well to navigate the tortuous coronary vasculature. Wires with integrated distal sensors which accomplish this feat are inherently expensive to produce.

Prior art fluid lines which provide a phasic pressure signal are typically underdamped and have a diameter much larger than a guide wire. As an example, Model PXMK099 from the Edwards Critical Care division of Baxter Health Care in Irvine, Calif. consists of a pressure transducer with a six inch connecting pressure tube connected to a user supplied fluid filled tube. When the Baxter system is connected to a 0.014 inch hollow guide wire, the output signal is totally damped and only a flat line average pressure is displayed. This damping is due to the relatively high compliance of the Baxter system and the relatively large volume of water contained therein. To determine the minimum tube diameter which can transmit a phasic blood pressure signal through the Baxter system, 1.8 m long polyimide tubes of varying diameters ranging from 0.012–0.057 inches were connected via a Touey-Borst style connector to the Baxter system. Experiments on this system found an average system compliance of $$\frac{dV}{dp} = 4 \times 10^{-14} m^5/NT (m^3/Nt/m^2)$$

and that the natural frequency was greater than or equal to 30 Hz in lines with diameters greater than 0.053" (0.0013 m). The lines with diameters less than 0.020 inches were over-damped and the lines with diameters larger than 0.020 inches were under-damped. Clearly prior art fluid lines which provide adequate frequency response are much larger than guide wires and still are not critically damped.

Another prior art device is disclosed by Tremulis in U.S. Pat. No. 4,953,553. Tremulis discloses a small diameter fluid filled line which can be used as a guide wire. However, blood pressure signals from this device may be extremely damped, giving only an average pressure value.

Therefore, it would be advantageous to provide a medical pressure sensing device with the reduced cost attributes of a fluid line, a small enough diameter to be used as a guide wire or to be used in small vessels, and sufficiently responsive to provide a phasic pressure signal.

SUMMARY OF THE INVENTION

The present invention overcomes the deficiencies of the prior art by providing a medical pressure sensing device which may be used as a guide wire, is inexpensive, and responsive enough to measure a phasic pressure signal. A first embodiment of the invention has a tube with an interior diameter of less than 0.0013 m. A pressure transducer is connected to the tube and is in fluid communication with the interior of the tube. Fluid pressure changes at the distal end of the tube are communicated to the pressure transducer at the proximal end of the tube. The system compliance is sufficiently low to measure a phasic signal. In particular the system compliance $$C < \left(\frac{D}{4f_0}\right)^2 \times \frac{1}{\pi\rho} \text{ and } C < \left(\frac{\xi D^3}{32\eta}\right)^2 \times \frac{\pi\rho}{L},$$

where the interior diameter D is less than 0.0013 meters, L is the length of the tube, $\rho$ is the density of the fluid, $\eta$ is the viscosity of the fluid, $f_0$ is the natural frequency of the system, and $\xi$ is the damping coefficient of the system.

Another embodiment of the medical pressure sensing device is tube which is about 1–4 meter long and has an inner diameter of less than about 0.0013 m. There is less than about 1 cc of fluid within the tube which transfers pressure changes from the distal end of the tube to a proximal pressure proximal pressure transducer. The total compliance of the system is less than about $4 \times 10^{-14}$ m$^5$/Nt. There may also be less than 0.004 cc of air trapped within the tube and the transducer.

The connector described in the previous embodiments may be a separate piece which may be connected to a medical fluid line. Examples of medical fluid lines include guide wires, catheters, needles, etc. The connector may further include a flush port and a stop cock. The total compliance of the connector and the pressure transducer may be less than $4\times10^{-14}$ m$^5$/Nt. Alternatively, the pressure transducer may be a light source aligned to direct light through the pressure sensing device coupled with a photodetector which is aligned to detect light directed through the fluid line. The light source may be a laser diode and it may be infrared light.

In use, the embodiments of the medical pressure sensing device described above may be inserted into a vessel and advanced to a position where the pressure is desired to be measured. The phasic pressure may then be measured or an average may be computed to provide a pressure measurement. A catheter may then be advanced over the medical pressure sensing device and therapeutic procedures may be conducted. The phasic pressure can be monitored during therapeutic procedures or before and after to determine efficacy of the procedures. The pressure sensing device may also be moved within the vessel to determine the change in pressure measurement across a specific section of the body lumen.

DETAILED DESCRIPTION OF THE INVENTION

Figure 1:
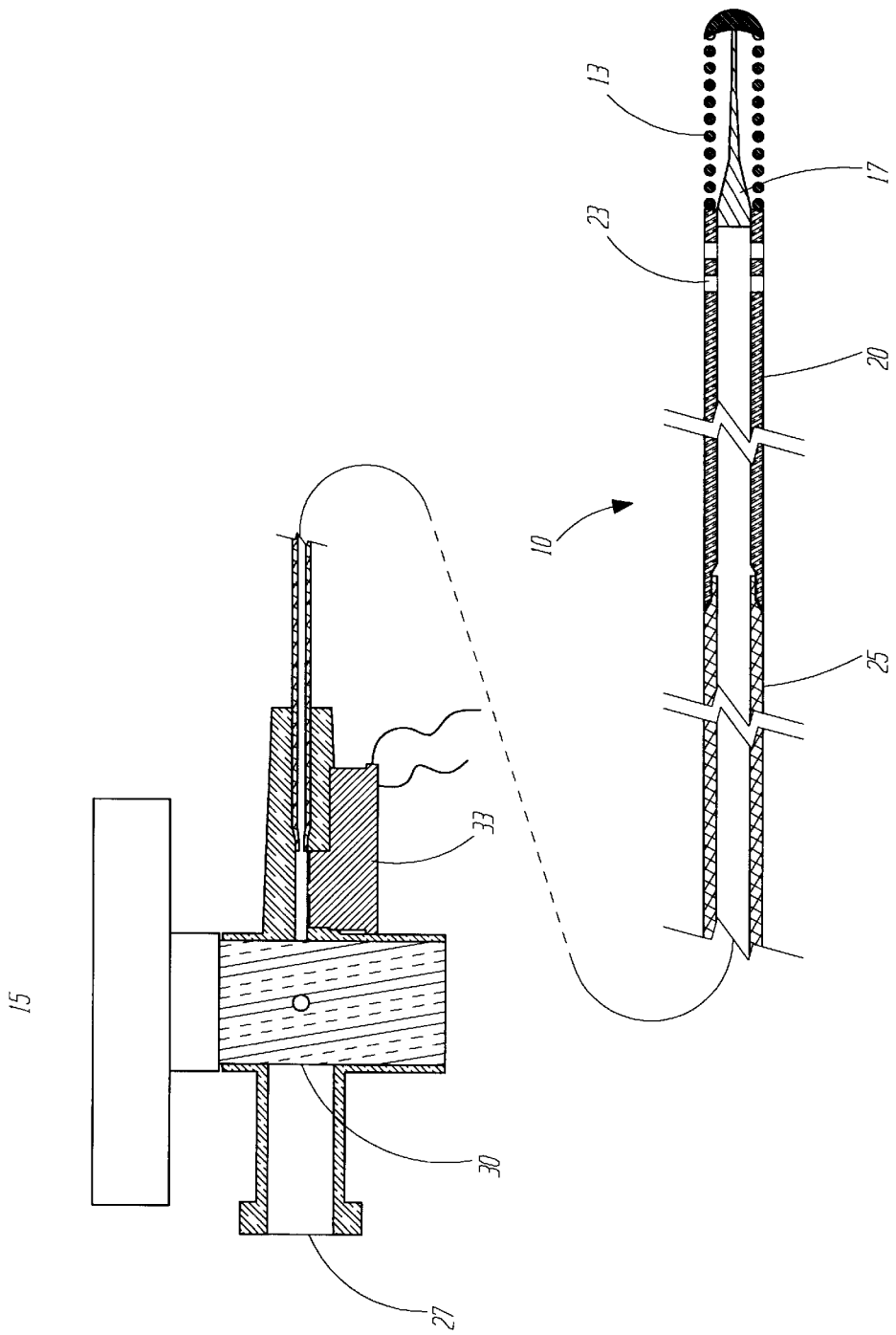
FIG. 1 depicts a side view of an embodiment of the invention.

The following detailed description should be read with reference to the drawings in which like elements in different drawing are numbered identically. The drawings, which are not necessarily to scale, depict selected embodiments and are not intended to limit the scope of the invention.

Examples of constructions, materials, dimensions, and manufacturing processes are provided for selected elements. All other elements employ that which is known to those skilled in the field of the invention. Those skilled in the art will recognize that many of the examples provided have suitable alternatives that may also be used.

A coronary guide wire is an ideal device for measuring pressure. It is the first catheter placed into the artery, and the last to be removed. In addition, since coronary guide wires are typically 0.014 inches in diameter, they are also sufficiently smaller than the arteries being treated. Unfortunately, prior art devices described above are too expensive or do not provide adequate signal fidelity. For this reason it is desirable to have a high fidelity fluid line connecting the distal and proximal ends of a guide wire, with a pressure sensor located outside the body where there is ample space to determine pressures at lower cost.

Fluid filled lines have been thoroughly studied and modeled in the past. A fluid line and pressure transducer system are modeled as a simple harmonic oscillator with the mass of fluid in the line, fluid resistance provided by the viscosity of the fluid assuming laminar flow, and restoring force provided by the system compliance. The frequency response of the pressure transducer is then given as a fraction of its dc value by the expression $$\frac{A}{A_0} = \frac{1}{\sqrt{[(f/f_0)^2 - 1]^2 + 4\xi(f/f_0)^2}}.$$

The natural frequency $f_0$ can be expressed by the equation $$f_0 = \frac{D}{4}\sqrt{\frac{1}{\pi C \rho}}.$$

The total system compliance C equals the sum of the compliance of each of the components in the system, $$C = \left(-\frac{dV}{dP}\right) = \Sigma(C_f + C_t)$$

in MKS units, where $C_f$ equals the compliance of the fluid, any materials that come in contact with the fluid, and any air in the system and $C_t$ equals the compliance of the transducer and any connecting apparatus. The system damping coefficient may be expressed by the equation $$\xi = \frac{32\eta}{D^3}\sqrt{\frac{LC}{\pi\rho}}.$$

| Symbol | Variable | Units |
|---|---|---|
| L | tube length | meters |
| $\xi$ | system damping coefficient | NA |
| $f_0$ | natural frequency | HZ |
| $\rho$ | density of the liquid | kg per cubic meter |
| $A_0$ | amplitude when $f = 0$. | MKS |
| A | signal amplitude | MKS |
| $f$ | frequency | HZ |
| C | system compliance | meters$^5$ per Newton (m$^3$/Nt/m$^2$) |
| $\eta$ | fluid viscosity | NtS/m$^2$ |

Commercially available fluid lines which are used to measure patient arterial or venous blood pressure during surgery typically have diameters of a few millimeters or larger and a natural frequency on the order of 30 Hz. Since the natural frequency is proportional to diameter and inversely proportional to the square root of compliance, a guide wire fluid line with a diameter equal to a fraction of a millimeter must have a dramatically reduced system compliance to maintain a 30 Hz or larger bandwidth. Similarly, the damping coefficient depends on the inverse cube of the fluid column diameter with larger diameter conventional lines under damped ($\xi<1$). To prevent over damping in small guide wire fluid lines, the compliance of the system must also be dramatically reduced.

Experimental work has confirmed the theoretical work which suggests that the compliance of a hollow 0.014 inch guide wire and a proximal pressure transducing apparatus are crucial to the frequency response of the phasic pressure wave. Any soft plastic or rubber materials present, even in small quantities anywhere in the system, can dampen the signal. Wherever possible, minimally compliant materials may then be used. Small amounts of air trapped in the system can also dampen the signal. To achieve adequate bandwidth and a damping coefficient less than unity, the amount of entrapped air should be less than 0.007 mm$^3$. In addition, typical commercially available pressure transducers contain compliant adhesives and gels, which also dampen the signal. If necessary custom pressure transducers may be manufactured. Finally, it has been determined that the total fluid volume of the system should be minimized (less than about 0.1 cc) to transmit good phasic signals. This is because water in a fluid line and connector has a very small but not negligible compliance which is proportional to the total volume of water in the system.

Refer now to FIG. 1 which depicts a body portion 10. A spring tip 13, as is commonly known in the art, is attached to the distal end of body portion 10. Spring tip 13 may have a safety ribbon 17 and may be about 1–4 cm long and is preferably about 3 cm long. Distal tube 20 may be formed of a super elastic material. The proximal end of safety ribbon 17 may be press fit into distal tube 20, soldered to distal tube 20, or preferably distal tube 20 is chilled into its Martensite phase and then ribbon 17 fit into place. When distal tube 20 is allowed to return to ambient temperature a compressive bond is formed.

Distal tube 20 maybe be any medical grade super elastic material and preferably is Nitinol with an Austinite finish temperature of 10° C.±10 as supplied by Raychem Corp. of California or the Nitinol Device Corp of California. The outside diameter of distal tube 20 may be about 0.0136 inches, the inside diameter may be about 0.0075 inches, and the length may be about 12 inches. Near the distal end of distal tube 20 are holes 23. There may be as few as one hole 23 but preferably there are about 6 holes 23 arranged in a helical pattern around distal tube 20 and spaced along an axial length of 0.020–0.040 inches. While no more than one hole 23 is required to provide a phasic pressure signal, several holes 23 ensure that the vessel wall or other material does not plug distal tube 20. Holes 23 may be electron discharge milled into distal tube 20 and electro-etched to remove any burrs. The exterior of the distal end of distal tube 20 may be further electro-etched to increase the flexibility of distal tube 20.

Alternatively, distal tube 20 may be made of a polymer/wire composite (not shown) as disclosed in WO 93/20881 to Pray et al., which is herein incorporated by reference. There may be one or more wires arranged in one of a variety of different patterns such as helix. This alternative distal tube 20 may be more flexible than a Nitinol distal tube 20 while maintaining a minimally compliant fluid path and the performance characteristics of a coronary guide wire.

The distal end of proximal hypotube 25 is bonded to the proximal end of distal tube 20. Proximal hypotube 25 may be press fit into distal tube 20, soldered to distal tube 20, or bonded in the method previously described. The joint between proximal hypotube 25 and distal tube 20 may be a stepped joint. However, to reduce the likelihood of breakage an angled joint as shown in FIG. 1 is preferred. Proximal hypotube 25 may be made of any medical grade alloy and is preferably made of 304V stainless steel which may be heat treated for resilience and plug drawn for smoothness. The inside diameter of proximal hypotube 25 may be about 0.0075 inches, the outside diameter about 0.0136 inches, and the length about 60 inches.

Flushing connector 15 may be bonded to the proximal end of proximal hypotube 25 or flushing connector 15 may be adapted to be releasably connected to any physiological fluid line. Flushing connector 15 may have a flushing port 27 and a stop cock 30. Integrally formed with or bonded to flushing connector 15 is pressure transducer 33. Pressure transducer 33 may be a commercially available solid state pressure transducer such as Model #109 available from Lucas Nova Corporation, in Freemont, Calif. Alternatively a custom pressure transducer may be manufactured by modifying the Model #109 from Lucas Nova Corporation which reduces the RTV glue used to bond the sensor to the substrate. The pressure transducer 33 may have electrical leads suitable for connection to standard monitoring systems.

Figure 2:
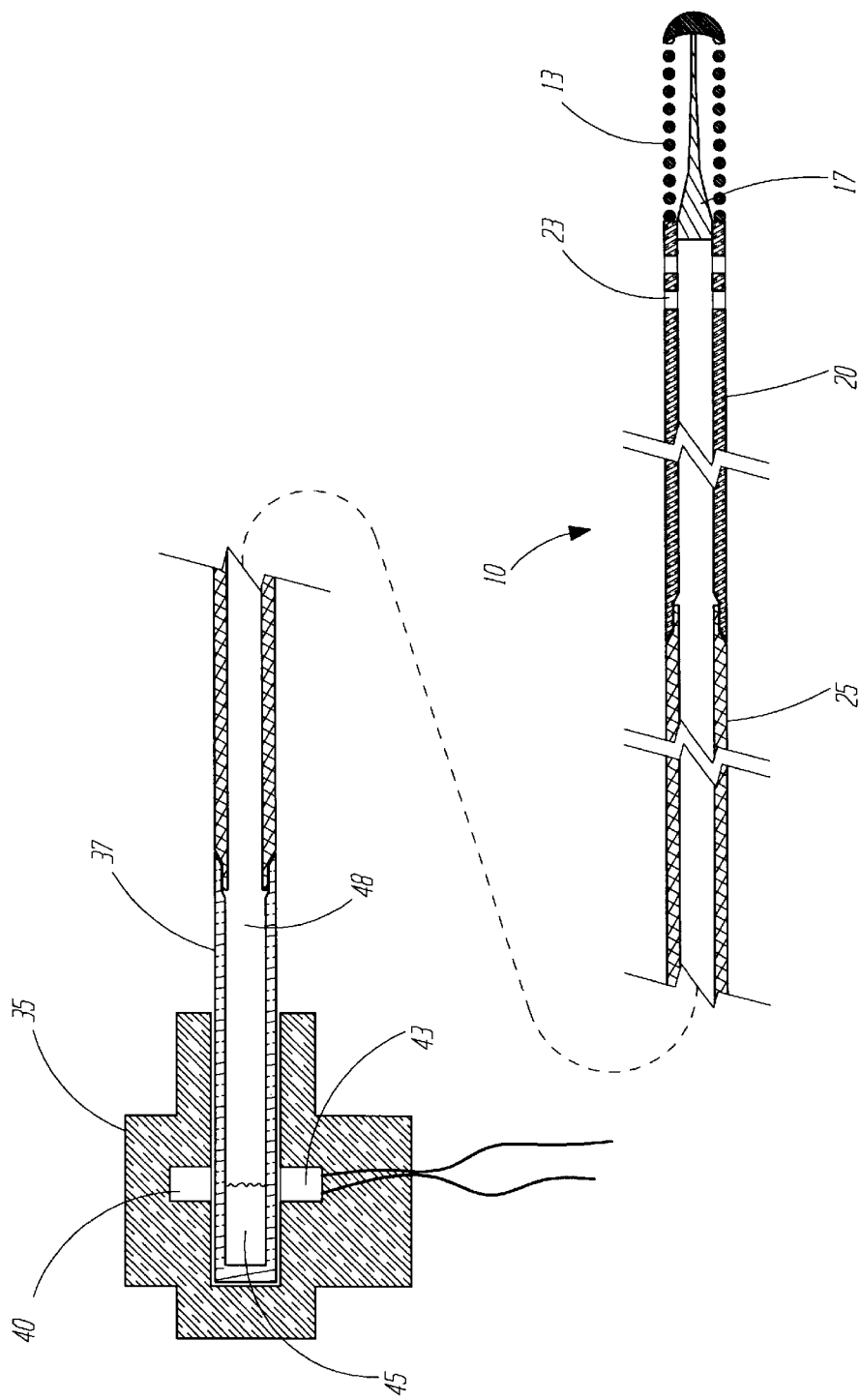
FIG. 2 depicts a side view of a second embodiment of the invention.

FIG. 2 depicts a second embodiment of the invention with body section 10 the same as previously described for the embodiment of FIG. 1. An optically clear view tube 37 is bonded to the proximal portion of proximal hypotube 25. View tube 37 may be made of glass, polyimide, a fused silica capillary as sold by Polymicro Technologies of Phoenix, Ariz., or any other optically clear minimally compliant material. Optical connector 35 may be bonded or releasably attached to the exterior of the proximal end of proximal hypotube 25 or may be adapted to be releasably connected to any physiological fluid line. Optical connector 35 houses a light source 40 which is aligned to shine through view tube 37. Light source 40 may be a light bulb with a lens or a laser diode but preferably is a light emitting diode. Light source 40 may produce a variety of wavelengths of light and will preferably produce infrared light. Optical connector 35 may also house a photodetector 43 aligned to receive light from light source 40 that has passed through view tube 37.

Within the proximal end of view tube 37 is an air column 45. Air column 45 is trapped by pressure communicating fluid 48. Pressure communicating fluid 48 may be any fluid which is bio-compatible, opaque to light from light source 40, minimally evaporative, and non-corrosive, examples of which may include ferrofluids, cotton seed oil, vegetable oil, saline, and water. The guide wire of this embodiment may be prepped prior to packaging. Specifically an air column 45 needs to be put in place in the proximal end of view tube 37, the pressure communicating fluid 48 loaded into view tube 37, and a temporary seal (not shown) placed around holes 23. The interface between the air column 45 and the pressure communicating fluid 48 must be aligned so as to cause a shadow between light source 40 and photodetector 43. Changes in fluid pressure at the distal end of the guide wire will cause the interface to move and the change in light detected by the photodetector can be interpreted as pressure changes. Preferably an air column which is about 0.01 inches long in a tube of 0.008 inches inside diameter is desired to give a compliance of about $8 \times 10^{-17}$ m$^5$/Nt and corresponds to a natural frequency of about 100 Hz and a damping coefficient of near unity. Further, the guide wire may be connected to a view tube 37 which has an outside diameter which is smaller than the inside diameter of the guide wire thereby allowing linear movement of the fluid column for a given change in distal pressure.

In use both of the embodiments described herein may be prepped by the manufacturer prior to packaging or by the user just prior to the procedure. When prepped by the user, the common technique of a positive prep may be used. This technique involves flushing fluid from the proximal end the guide wire, out of the distal end of the guide wire and thereby flushing any air from the system. A negative prep may also be used by creating negative pressure at the proximal end of the guide wire, as by a syringe, and drawing any air from the system while filling the guide wire with a fluid. Once prepped, the guide wire may be used in the same way as a conventional guide wire. That is, the wire is inserted into the vasculature and advanced to a desired treatment site. Once at the treatment site the guide wire, unlike common coronary guide wires, may be used to sense phasic pressure. Pressure may be sensed at different locations. For instance pressure can be measured on either side of a lesion. If a therapeutic procedure is desired, another device, like an angioplasty balloon catheter, may be advanced over the wire. Pressure may also be measured at different times such as during, before, or after a procedure.

While the specification describes the preferred designs, materials, methods of manufacture and methods of use, those skilled in the art will appreciate the scope and spirit of the invention with reference to the appended claims.

We claim:

1. A medical pressure sensor comprising:

a body portion having a proximal end, a distal end, and a lumen extending therethrough for communicating pressure from the distal end of the body portion to the proximal end of the body portion, the body portion having a compliance $C_f$ which includes the compliance of the body portion and any fluid therein; and a transducer positioned near the proximal end of the body portion and in fluid communication with the lumen, the transducer having a compliance $C_t$, where the system compliance $C=C_f+C_t$, and the system compliance $$C < \left(\frac{D}{4f_0}\right)^2 x \frac{1}{\pi \rho} \text{ and } C < \left(\frac{\xi D^3}{32\eta}\right)^2 x \frac{\pi \rho}{L}$$

where the diameter D is less than about 0.0013 meters, the natural frequency $f_0$ less than about 30 Hz, $\pi$ is a constant equal to 22/7, $\rho$ is the density of the fluid in kilograms per cubic meter, $\eta$ is the fluid viscosity in newton seconds per square meter, L is the length of the lumen in meters, and the system damping coefficient $\xi$ is less than about 3.0.

2. A pressure sensing device having a total compliance, the device comprising:

an elongate body having length of about 1–4 meters, a pressure communicating lumen extending therethrough, an inner diameter of less than about 0.0013 meters, and a proximal end; and a transducer attached to the proximal end of the elongate body and in fluid communication with the lumen, the total compliance of the pressure sensing device less than about $4 \times 10^{-14}$ m$^5$/Nt.

3. The pressure sensing device of claim 2 wherein the total compliance of the device includes the compliance of a volume of liquid disposed thereon, the volume of liquid being less than about one cubic centimeter.

4. The pressure sensing device of claim 2 wherein the total compliance of the device includes the compliance of a volume of entrapped air disposed thereon, the volume of entrapped air being less than about 0.004 cubic centimeters.

5. A method of sensing a phasic pressure signal within a body lumen comprising:

providing an elongate body having a proximal end, a distal end, a pressure communicating lumen therethrough, a fluid within the pressure communicating lumen, a transducer attached to the proximal end of the elongate body and in fluid communication with the pressure communicating lumen, and a system compliance of less than about $4 \times 10^{-14}$ m$^5$/Nt, the pressure communicating lumen having a diameter of less than about 0.0013 meters;

inserting the distal end of the elongate body into the body lumen;

advancing the elongate body to a position within the body lumen; and sensing the phasic pressure signal at that position within the body lumen.

6. The method of sensing a phasic pressure signal within a body lumen of claim 5 further comprising:

providing a catheter having a lumen therethrough; and advancing the catheter over the elongate body after the elongate body has been advanced to the position within the body lumen.

7. The method of sensing a phasic pressure signal within a body lumen of claim 6 further comprising:

conducting a therapeutic procedure with the catheter after the catheter has been advanced to the position within the body; and sensing the phasic pressure signal before, during or after the therapeutic procedure has been conducted.

8. The method of sensing a phasic pressure signal within a body lumen of claim 7 further comprising:

sensing the phasic pressure signal before and after the therapeutic procedure.

9. A connector suitable for removeably connecting to a medical pressure sensing instrument, the connector comprising:

a body portion having an interior and a port suitable for providing fluid communication between the medical pressure sensing instrument and the interior of the body portion, the body portion having a compliance; and a pressure transducer attached to the body portion and in fluid communication with the interior of the body, the pressure transducer having a compliance, wherein the sum of the compliance of the body portion and the compliance of the pressure transducer is less than $4 \times 10^{-14}$ m$^5$/Nt.

10. The connector of claim 9 further comprising:

a flush port in fluid communication with the interior of the body portion; and stop cock positioned such that fluid communication between the interior of the body portion and the flush port may be blocked.

11. The connector of claim 9 wherein the pressure transducer comprises a solid state pressure transducer.

12. The connector of claim 9 wherein the pressure transducer comprises:

a light source attached to the body portion and aligned to shine through the medical pressure sensing instrument; and a photodetector attached to the body portion and positioned to detect light shined through the medical sensing instrument.

13. The connector of claim 12 wherein the light source comprises a light emitting diode.

* * * * *

UNITED STATES PATENT AND TRADEMARK OFFICE
CERTIFICATE OF CORRECTION

PATENT NO. : 5,860,938
DATED : January 19, 1999
INVENTOR(S) : Lafontaine et al.

It is certified that error appears in the above-identified patent and that said Letters Patent is hereby corrected as shown below:

On the title page: under "OTHER PUBLICATIONS," change "Theorectical" to --Theoretical--.

On first page, under "OTHER PUBLICATIONS," change "$3^{4rd}$" to --$3^{rd}$--.

At column 1, line 26, change "asses" to --assess--.

At column 2, lines 59-60, delete the second occurrence of "proximal pressure."

At column 3, line 3, "Alternatively" should start a new paragraph.

At column 3, line 37, change "drawing" to --drawings--.

At column 5, line 18, change "maybe" to --may--.

At column 6, line 51, insert --of-- after "end."

At column 8, claim 10, line 4, insert --a-- before "stop."

Signed and Sealed this

Seventeenth Day of April, 2001

*Attest:*

NICHOLAS P. GODICI

*Attesting Officer*     *Acting Director of the United States Patent and Trademark Office*